(12) United States Patent
Tang et al.

(10) Patent No.: US 11,813,081 B2
(45) Date of Patent: Nov. 14, 2023

(54) INTELLIGENT GLASSES AND GLASSES BOX

(71) Applicants: BEIJING XIAOMI MOBILE SOFTWARE CO., LTD., Beijing (CN); Lumos Health Inc., Waterloo (CA)

(72) Inventors: Lucas Wen Tang, Waterloo (CA); Jamie Marc Zeitzer, Waterloo (CA)

(73) Assignees: BEIJING XIAOMI MOBILE SOFTWARE CO., LTD., Beijing (CN); Lumos Health Inc., Waterloo (CA)

( * ) Notice: Subject to any disclaimer, the term of this patent is extended or adjusted under 35 U.S.C. 154(b) by 238 days.

(21) Appl. No.: 17/167,856

(22) Filed: Feb. 4, 2021

(65) Prior Publication Data

US 2021/0386372 A1    Dec. 16, 2021

(30) Foreign Application Priority Data

Jun. 15, 2020    (CN) .......................... 202010543453.4

(51) Int. Cl.
*A45C 11/04*    (2006.01)
*A61M 21/00*    (2006.01)
(Continued)

(52) U.S. Cl.
CPC ............ *A61B 5/6803* (2013.01); *A45C 11/04* (2013.01); *A45C 15/00* (2013.01); *A61B 5/0205* (2013.01);
(Continued)

(58) Field of Classification Search
CPC . A61B 5/6803; A45C 11/04; A61M 21/00–02
See application file for complete search history.

(56) References Cited

U.S. PATENT DOCUMENTS

RE39,539 E    4/2007  Torch
RE41,376 E    6/2010  Torch
(Continued)

FOREIGN PATENT DOCUMENTS

CA        3 011 327 A1    8/2017
KR   10-2017-0009658 A    1/2017

OTHER PUBLICATIONS

Office Action dated Mar. 8, 2022, in corresponding Canadian Patent Application No. 3,109,295, 4 pages.
(Continued)

*Primary Examiner* — Thaddeus B Cox
(74) *Attorney, Agent, or Firm* — Oblon, McClelland, Maier & Neustadt, L.L.P.

(57) ABSTRACT

The present disclosure relates to a pair of intelligent glasses and a glasses box. The intelligent glasses can include a frame assembly having an inner frame portion and an outer frame portion that is arranged around the inner frame portion, a detection component configured to detect physiological characteristics of a wearer, a control component connected with the detection component and configured to acquire a control signal generated according to the physiological characteristics and a treatment component, connected with the control component and configured to output treatment signals according to the control signal. One or more accommodating spaces are formed between the inner frame portion and the outer frame portion. The treatment signals include at least one of a phototherapy signal, a sonic wave signal, a sound wave signal, magnetic waves, or electromagnetic waves. The detection component, the control component and the treatment component are located in the accommodating spaces.

19 Claims, 2 Drawing Sheets

(51) Int. Cl.
  *A61B 5/1455*    (2006.01)
  *A61B 5/00*      (2006.01)
  *A45C 15/00*     (2006.01)
  *A61B 5/0205*    (2006.01)
  *A61B 5/16*      (2006.01)
  *G02C 5/14*      (2006.01)
  *G02C 1/00*      (2006.01)
  *A61B 5/369*     (2021.01)
  *A61B 5/389*     (2021.01)
  *A61B 5/332*     (2021.01)
  *A61B 3/113*     (2006.01)
  *A61B 3/14*      (2006.01)

(52) U.S. Cl.
  CPC ............ *A61B 5/165* (2013.01); *A61B 5/4836* (2013.01); *A61M 21/00* (2013.01); *G02C 1/10* (2013.01); *G02C 5/14* (2013.01); *A61B 3/113* (2013.01); *A61B 3/14* (2013.01); *A61B 5/14552* (2013.01); *A61B 5/332* (2021.01); *A61B 5/369* (2021.01); *A61B 5/389* (2021.01); *A61B 5/4266* (2013.01); *A61M 2021/0027* (2013.01); *A61M 2021/0044* (2013.01); *A61M 2021/0055* (2013.01)

(56) References Cited

U.S. PATENT DOCUMENTS

| | | |
|---|---|---|
| RE42,471 E | 6/2011 | Torch |
| 9,579,060 B1* | 2/2017 | Lisy .................. A61B 5/165 |
| 2013/0214998 A1 | 8/2013 | Andes et al. |
| 2014/0213917 A1* | 7/2014 | Hobeika ............ A61B 5/02438 600/500 |
| 2017/0242497 A1 | 8/2017 | Andes et al. |
| 2018/0122208 A1* | 5/2018 | Peyrard .................. A61B 5/163 |
| 2019/0000357 A1* | 1/2019 | Ross .................... A61B 5/0531 |
| 2020/0008687 A1* | 1/2020 | Friedlander ............ A61B 5/064 |
| 2020/0094015 A1 | 3/2020 | Colbaugh et al. |
| 2022/0179213 A1* | 6/2022 | Zhou ........................ H02J 50/90 |

OTHER PUBLICATIONS

Extended European Search Report dated Jul. 6, 2021 in European Patent Application No. 21151915.2, 8 pages.

* cited by examiner

INTELLIGENT GLASSES AND GLASSES BOX

CROSS-REFERENCE TO RELATED APPLICATIONS

This application is based upon and claims priority to Chinese Patent Application No. CN202010543453.4, filed Jun. 15, 2020, the entire contents of which are incorporated herein by reference.

TECHNICAL FIELD

The present disclosure relates to the technical field of intelligent glasses, including intelligent glasses and a glasses box.

BACKGROUND

Mental diseases, such as depression, anxiety and bipolar disorder have become the world's most common diseases. In recent years, the number of depression patients in the world has increased by 18%. Usually these mental disease problems are discovered and treated by professional psychologists. Existing professional psychologists request a lot of waiting time to solve the mental disease problems. At the same time, existing electronic equipment is not convenient to carry and has only a single function. Generally, functions realized by the electronic equipment, such as a communication function, an entertainment function and/or a simple physiological monitoring function, cannot prevent and solve the mental disease problems well.

SUMMARY

The present disclosure provides intelligent glasses and a glasses box. A first aspect of the present disclosure provides a pair of intelligent glasses that can include a frame assembly having an inner frame portion and an outer frame portion arranged around the inner frame portion, one or more accommodating spaces are formed between the inner frame portion and the outer frame portion. Further, the glasses can include a detection component that is configured to detect physiological characteristics of a wearer, and a control component that is connected with the detection component and configured to acquire a control signal generated according to the physiological characteristics. Additionally, the glasses can include a treatment component that is connected with the control component and configured to output treatment signals according to the control signal, the treatment signals include at least one of a phototherapy signal, a sonic wave signal, a sound wave signal, magnetic waves or electromagnetic waves. Each of the detection component, the control component and the treatment component is located in the accommodating space.

A second aspect of the present disclosure provides a glasses box. The glasses box cooperates with the intelligent glasses in the first aspect. The glass box can include a charging component. The charging component cooperates with the intelligent glasses to charge the intelligent glasses through the glasses box.

It should be understood that the above general description and the following detailed description are exemplary and explanatory only, and are not intended to limit the present disclosure.

BRIEF DESCRIPTION OF THE DRAWINGS

The accompanying drawings, which are incorporated in and constitute a part of this specification, illustrate embodiments consistent with the invention and, together with the description, serve to explain the principles of the invention.

DETAILED DESCRIPTION

Exemplary embodiments will be described in detail herein, examples of which are illustrated in the accompanying drawings. When the following description refers to the accompanying drawings, the same numbers in different drawings represent the same or similar elements unless otherwise indicated. The implementations described in the following exemplary embodiments do not represent all implementations consistent with the present disclosure. Rather, they are merely examples of apparatuses and methods consistent with some aspects of the present disclosure as detailed in the appended claims.

Figure 1:
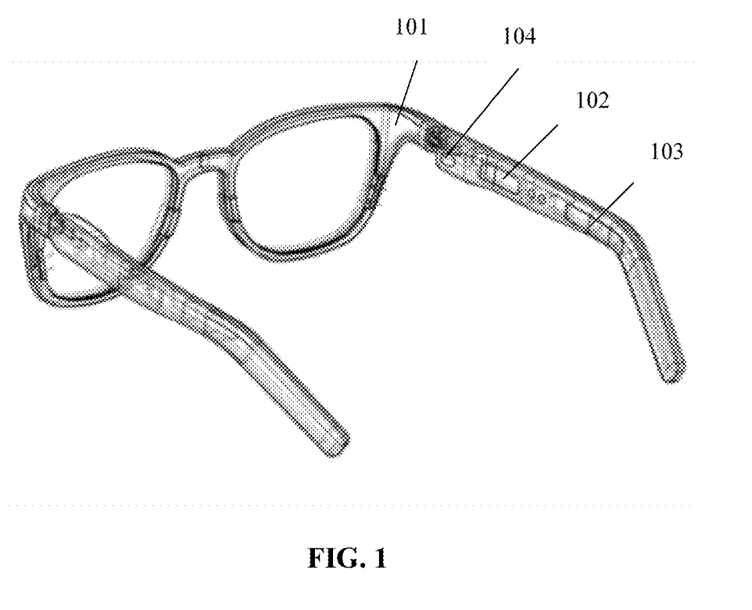
FIG. 1 is a schematic diagram of a pair of intelligent glasses according to an exemplary embodiment.
Figure 4:
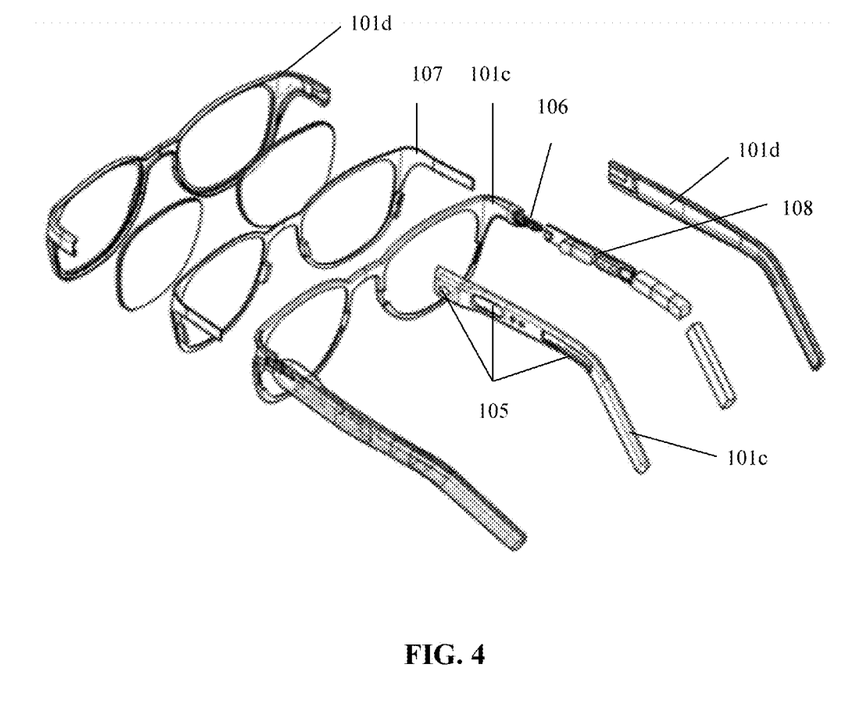
FIG. 4 is yet another schematic diagram of a pair of intelligent glasses according to an exemplary embodiment.

FIG. 1 is a schematic diagram of a pair of intelligent glasses according to an exemplary embodiment. FIG. 4 is a schematic diagram of a pair of intelligent glasses according to an exemplary embodiment. As shown in FIG. 1 and FIG. 4, the intelligent glasses can include a frame assembly 101, including an inner frame portion 101c and an outer frame portion 101d arranged around the inner frame portion, one or more accommodating spaces are formed between the inner frame portion 101c and the outer frame portion 101d. The intelligent glasses can also include a detection component 102 for detecting physiological characteristics of a wearer, and a control component 103 that is connected with the detection component and configured to acquire a control signal generated according to the physiological characteristics. Additionally, the intelligent glasses can include a treatment component 104 that is connected with the control component and configured to output treatment signals according to the control signal, the treatment signals include at least one of a phototherapy signal, a sonic wave signal, a sound wave signal, magnetic waves or electromagnetic waves.

Each of the detection component 102, the control component 103 and the treatment component 104 is located in the accommodating space.

In the embodiments of the present disclosure, the frame assembly is configured to support optical lens placed on the frame assembly. The frame assembly may be formed of metal, plastic, resin or other suitable material. The frame assembly includes an inner frame portion and an outer frame portion. After the glasses are worn, the inner frame portion faces towards the wearer or is in contact with the skin of the user, and the outer frame portion faces away from the wearer.

In the embodiments of the present disclosure, one or more accommodating spaces are formed between the inner frame portion and the outer frame portion. In the case that one accommodating space is formed between the inner frame portion and the outer frame portion, the accommodating space can be configured to accommodate a plurality of independent components. For example, the accommodating space can simultaneously accommodate the detection component, the control component and the treatment component. In the case that a plurality of accommodating spaces are formed between the inner frame portion and the outer frame portion, one accommodating space may accommodate one component, and then a plurality of accommodating spaces may accommodate a plurality of components; or, one accommodating space may accommodate a plurality of components which may be integrated with one another.

It should be noted that an accommodating cavity is formed between the inner frame portion and the outer frame portion, and the one or more accommodating spaces may be formed in the accommodating cavity.

In the embodiments of the present disclosure, the detection component, the control component and the treatment component are located in the accommodating spaces. The detection component, the control component and the treatment component may be located at different positions of one accommodating space, and may also be located in different accommodating spaces. The embodiments of the present disclosure are not limited thereto.

The detection component is configured to detect physiological characteristics of a wearer. The physiological characteristics of the wearer may reflect a physiological status of the wearer. The physiological status may be physical and mental health statuses of the wearer.

It should be noted that the detection component may include at least one detection sensor, and the different detection sensors are configured to detect different physiological characteristics. For example, an eyeball detection sensor may detect eyeball motion information in the physiological characteristics, a sweat detection sensor may detect sweat information in the physiological characteristics, a near infrared spectrum detection sensor may detect blood oxygen content information in the physiological characteristics, a heart rate detection sensor may detect a heart rate in the physiological characteristics, and a body mass index (BMI) detection sensor may detect metabolism velocity information in the physiological characteristics. The embodiments of the present disclosure are not limited thereto.

In the embodiments of the present disclosure, the detection component may further include an image collection component, such as a visible light image collection component and an infrared image collection component. The physiological characteristics can also be obtained through image collection and image analysis. The control component acquires a control signal generated according to the physiological characteristics. The control signal may be configured to control the treatment component to output treatment information, and may also be configured to control components other than the treatment component, to execute corresponding operations.

In some embodiments, when the physiological characteristics reflect that the current physical and mental status of the wearer is abnormal (when an unhealthy physiological phenomenon occurs), the control signal may be configured to control the treatment component to output treatment signals, when the physiological characteristics reflect that the current physical and mental status of the wearer is normal (i.e., healthy), the control signal may be configured to control the treatment component to stop outputting treatment signals.

In some other embodiments, the intelligent glasses further include a voice output component. When the physiological characteristics reflect that the current physical and mental status of the wearer is a normal status, the control signal acquired by the control component may be configured to control the voice output component to output a normality voice prompt; and when the physiological characteristics reflect that the current physical and mental status of the wearer is an abnormal status, the control signal acquired by the control component may be configured to control the voice output component to output an abnormality voice prompt.

In the embodiments of the present disclosure, the treatment component includes at least one of: a light source sub-component, a sonic wave emission sub-component, a sound wave emission sub-component or a magnetic wave sub-component. The light source sub-component is configured to emit the phototherapy signal, the sonic wave emission sub-component is configured to emit the sonic wave signal, the sound wave emission sub-component is configured to emit the sound wave signal, and the electromagnetic wave sub-component is configured to emit the magnetic waves or the electromagnetic waves.

It should be noted that the treatment component may further include an electrode sub-component, and the electrode sub-component is configured to emit an electrical signal to the wearer, so as to achieve a treatment effect.

The treatment signals may be applied for treating brain diseases, mental diseases (such as depression or anxiety) or eye fatigue. For example, the phototherapy signal includes an ultrasonic signal, a visible light signal, an infrared signal and a laser signal. The brain diseases or the mental diseases may be treated through the phototherapy signal. The mental diseases may be treated through the sound wave signal and the sonic wave signal, and the headache or fatigue may be relieved through the sound wave signal and the sonic wave signal. The magnetic waves or electromagnetic waves can promote the wearer's absorption of the elements that is deficient for the wearer, or can effectively promote cerebral blood circulation.

It should be noted that the control signal may be configured to control one or more treatment components to output one or more treatment signals. For example, the control signal may control the treatment component to output the phototherapy signal, or may control the treatment component to simultaneously output the phototherapy signal and the sonic wave signal. The embodiments of the present disclosure are not limited thereto.

It can be understood that in the embodiments of the present disclosure, the physiological characteristics of the wearer are detected by means of the detection component. Subsequently, the control signal is generated based on the physiological characteristics. Finally, the treatment signals are output through the treatment component. That is, the intelligent glasses of the embodiments of the present disclosure are integrated with both the detection and the treatment, and can pre-diagnose the abnormal status of the wearer in advance, and treat the user in time when the detected physiological characteristics reflect that the wearer is in the abnormal status. In this way, the intelligent glasses are multifunctional and more intelligent, and the timeliness of treatment can also be improved. At the same time, the treatment signals output by the treatment component can include the phototherapy signal, the sonic wave signal, the sound wave signal, the magnetic waves and the electromagnetic waves, so that treatment behaviors for the wearer can be enriched through the various different treatment signals, and different treatment therapies can also be customized for different users to enhance the treatment effect.

In some embodiments, the detection component may include at least one of an eyeball detection sensor, including an infrared emitter and an infrared collector, wherein the infrared emitter is configured to emit infrared light, the collector is configured to collect infrared light reflected by an eyeball, and determining, based on the reflected infrared light, eyeball motion information in the physiological characteristics. Further, the detection component can include a sweat detection sensor that is configured to detect sweat information in the physiological characteristics, a near infrared spectrum detection sensor, configured to detect blood oxygen content information in the physiological characteristics, and an electrode detection sensor that is configured to detect electric wave information in the physiological characteristics.

In the embodiments of the present disclosure, the detection component may include at least one of the eyeball detection sensor, the sweat detection sensor, the near infrared spectrum detection sensor and the electrode detection sensor. For example, the detection component may include the eyeball detection sensor and the sweat detection sensor, or may include the eyeball detection sensor, the sweat detection sensor and the near infrared spectrum detection sensor. The embodiments of the present disclosure are not limited thereto.

The eyeball motion information includes a gazing direction of eyeballs, a gazing target of the eyeballs or pupil change information. The embodiments of the present disclosure are not limited thereto. It should be noted that, in the pupil change information, the sizes of the pupils vary along with the change in the mood, so that the physical and mental status of the wearer can be determined by detecting the sizes of the pupils, and then the treatment component is controlled in time to output the treatment signals when it is detected that the physical and mental status is abnormal.

The sweat information includes a sweat amount, a sweat concentration, and various substances, such as electrode, metabolites, amino acids and protein, contained in sweat. The sweat information is detected to determine the physical and mental status of the wearer, and then the treatment component is controlled in time to output the treatment signals when it is detected that the physical and mental status is abnormal.

The blood oxygen content information includes hemoglobin content information and deoxyhemoglobin content information. The blood oxygen content information is detected to acquire a brain activity of the wearer. When it is detected that the brain activity is abnormal, the treatment component can be controlled in time to output the treatment signals.

The electrode detection sensor includes but is not limited to: an electrocardiogram (ECG) detection sensor, an electromyogram detection sensor and an electroencephalogram (EEG) sensor. The ECG detection sensor is configured to detect an electrocardiogram of the wearer; the electromyogram detection sensor is configured to detect an electromyogram of the wearer; and the EEG sensor is configured to detect brain waves of the wearer. It should be noted that the physical and mental status of the wearer can be determined by means of one or more of the electrocardiogram, the electromyogram and the brain waves. For example, whether the wearer suffers from depression or whether the wearer is in a low mood can be determined by means of one or more of the electrocardiogram, the electromyogram and the brain waves.

It can be understood that one or more detection sensors in the detection component are arranged on the intelligent glasses, and can directly collect data in daily wearing, so that the collected data is more convenient and abundant. Furthermore, when the detection component includes the various detection sensors, the intelligent glasses can simultaneously detect various physiological characteristics such as the eyeball motion information, the sweat information, the blood oxygen content information and the brain wave information, and can reflect the physical and mental status of the wearer more accurately by combining the various different physiological characteristics and then output more accurate treatment signals, thus improving the treatment effect.

Figure 2:
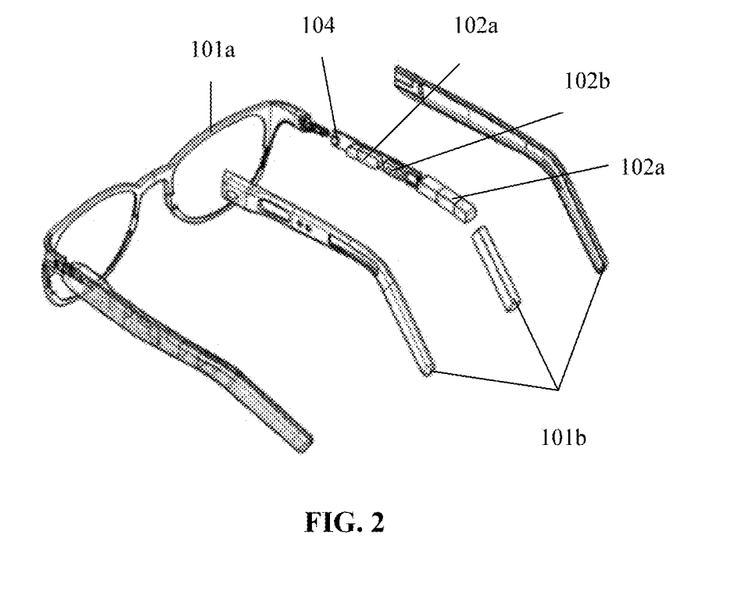
FIG. 2 is another schematic diagram of a pair of intelligent glasses according to an exemplary embodiment.

In some embodiments, as shown in FIG. 2, the frame assembly can include a lens frame 101a and a leg 101b hinged to the lens frame 101a. The near infrared spectrum detection sensor 102b, the electrode detection sensor 102a and the treatment component 104 are distributed in different accommodating spaces at the leg. The treatment component 104 is located in the accommodating space at an end portion of the leg 101b. The electrode detection sensor 102a is located between the treatment component 104 and the near infrared spectrum detection sensor 102b.

In the embodiments of the present disclosure, the lens frame is for mounting optical lens; and the leg may be unfolded or folded relative to the lens frame. For example, during wearing, the leg is unfolded relative to the lens frame; and after the wear, the leg is folded relative to the lens frame. In this way, the intelligent glasses can be convenient to carry and store.

In the embodiments of the present disclosure, the treatment component may generate a phototherapy signal. For therapeutic purposes, the phototherapy signal is required to be emitted into eyes. Therefore, the leg may be disposed at a position near to the lens frame to cause the treatment component to be close to the eye of the wearer, thus improving the treatment effect of the treatment signal.

In some embodiments, as shown in FIG. 2, two electrode detection sensors 102a may be provided. The near infrared spectrum detection sensor 102b is located between the two electrode detection sensors 102a.

It can be understood that the embodiments of the present disclosure may obtain more accurate electric wave information of the wearer by means of analyzing and comparing electric wave information detected by the two electrode detection sensors, so as to improve the precision of detection.

Figure 3:
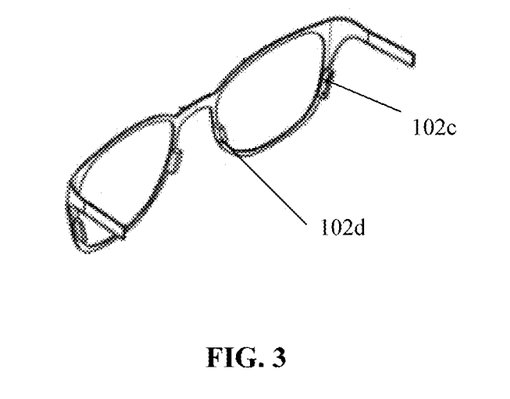
FIG. 3 is yet another schematic diagram of a pair of intelligent glasses according to an exemplary embodiment.

In some embodiments, as shown in FIG. 3, the frame assembly includes: at least one lens frame, and a leg connected to one side of the lens frame and a nose pad connected to another side of the lens frame. The eyeball detection sensor 102c may be located in the accommodating space at the at least one lens frame, and is located on the side of the lens frame where the leg is located. The sweat detection sensor 102d may be located in the accommodating space at the nose pad.

The frame assembly may include one lens frame or two lens frames. In the case that the frame assembly includes two lens frames, each of the two lens frames is provided with the eyeball detection sensor. In this way, by means of arranging the eyeball detection sensors at the positions close to the glasses, better detection of the eyeball motion information can be realized. Furthermore, two eyeball detection sensors are provided, so that, more accurate eyeball motion information can be obtained by means of comparing and analyzing the information detected by the two eyeball detection sensors, thus improving the precision of detection.

In the embodiments of the present disclosure, the frame assembly may include two lens frames, and two corresponding legs and two nose pads may be respectively connected to two sides of the lens frames. During wearing of the intelligent glasses, the nose pads are in contact with the nose of the wearer.

The sweat detection sensor is configured to detect the sweat information. The nose is a place, where sweats are produced easily, of the wearer. Therefore, the sweat detection sensors are arranged on the nose pads to enable the sweat detection sensors to precisely detect the sweat information. In some embodiments, the sweat detection sensor may be detachably connected to the nose pad.

The above-mentioned detachable connection of the sweat detection sensor and the nose pad includes threaded connection, snap connection or hinged connection. The embodiments of the present disclosure are not limited thereto.

It can be understood that, the sweat detection sensor is detachably connected to the nose pad, so that the sweat detection sensor can be convenient to replace from the nose pads when the sweat detection sensor is damaged due to hidropedesis.

In some embodiments, as shown in FIG. 4, the inner frame portion 101c may have an opening 105. The detection component may send a detection signal to the wearer through the opening, or detection component may receive, through the opening, a detection signal returned from the wearer.

In the embodiments of the present disclosure, the inner frame portion may have one or more openings. For example, a plurality of detection components located on the leg may share one opening on the leg to output detection signals or receive returned detection signals. Each of the plurality of detection components on the leg may also output the detection signals or receive the returned detection signals through the respective one of the openings. The embodiments of the present disclosure are not limited thereto.

It should be noted that when there are a plurality of detection components, the number of the openings may be the same as the number of detection sensors in the detection components.

It can be understood that by providing the opening on the inner frame portion, better outputting of the detection signals and better receiving of the returned detection signals can be realized, which enable the detection components to detect signals better.

In some embodiments, the intelligent glasses further include a connector having a first connection member and a second connection member hinged to the first connection member.

The frame assembly includes a lens frame connected with the first connection member and a leg connected with the second connection member, wherein, when the connector is folded at a hinged location of the first connection member and the second connection member, the leg can be folded relative to the lens frame.

It should be noted that the connector may also has a rotating shaft. Two first rotating holes spaced apart one from the other are formed in the first connection member, and one second rotating hole is formed in the second connection member. The second rotating hole is located between the two first rotating holes. The rotating shaft passes through the first rotating holes and the second rotating hole in sequence. Thus, the first connection member and the second connection member can rotate around the rotating shaft to realize folding of the first connection member and the second connection member. Exemplarily, the connector includes, but is not limited to, a hinge.

It can be understood that, by providing the connector, when the connector is folded at a hinged location, the leg may be folded relative to the lens frame, so that the intelligent glasses can be convenient to store and carry.

In some embodiments, the intelligent glasses further include a first flexible printed circuit board covering the connector. The first flexible printed circuit board is folded along with the folding of the connector.

In the embodiments of the present disclosure, the expression "the first flexible printed circuit board covers the connector" means that the first flexible printed circuit board completely or partially covers the connector. When the connector is folded at the hinged location, the first flexible printed circuit board is folded along with the folding of the connector based on flexibility. In this way, the detection component arranged on the lens frame may realize the data transmission with the control component located on the leg through the first flexible printed circuit board.

In some embodiments, as shown in FIG. 4, the connector 106 includes a first connection port located on the first connection member, a second connection port located on the second connection member, and at least one connection line connected between the first connection port and the second connection port.

The intelligent glasses further can include a second flexible printed circuit board 107, located in the accommodating space at the lens frame and connected with the first connection port, and a third flexible printed circuit board 108, located in the accommodating space at the leg and connected with the second connection port.

In the embodiments of the present disclosure, the first connection member of the connector is provided with the first connection port, and the first connection port is configured to establish a connection with the second flexible printed circuit board (FPC); and the second connection member of the connector is provided with the second connection port, and the second connection port is configured to establish a connection with the third flexible printed circuit board.

The connector is also provided with at least one connection line for connecting the first connection port with the second connection port. The connection line, the first connection port and the second connection port together form a connection passageway to realize electrical connection between the second flexible printed circuit board on the lens frame and the third flexible printed circuit board, thus the data transmission from the detection component on the lens frame to the control component on the leg can be achieved.

It should be noted that the connector may be composed of a conductive wire and plastic. The conductive wire is made of metal or an alloy material. The embodiments of the present disclosure are not limited thereto. The conductive wire may form a connection line for allowing the electrical connection between the first connection port and the second connection port.

It can be understood that in the embodiments of the present disclosure, two flexible printed circuit boards may be arranged on the lens frame and the leg respectively, and electrical connection of the two flexible printed circuit board is realized through the connector. In some embodiments, the frame assembly includes a leg.

The intelligent glasses further includes a communication component, located on the leg, connected with the control component and configured to send the physiological characteristics detected by the detection component and receiving a detection result returned based on the physiological characteristics.

In the embodiments of the present disclosure, the communication component may be electrically connected with a cloud server. Detected data detected by the detection component is subjected to algorithm processing by the cloud server to obtain the detection result. It should be noted that the communication component may send the received detection result to the control component, and the control component generates a control signal based on the detection result.

Exemplarily, the communication component may employ any communication standard or component, such as a Bluetooth communication component, a Wi-Fi communication component, a 5G communication component or a 6G communication component, and may also include a near field communication (NFC) component. The embodiments of the present disclosure are not limited thereto.

In the embodiments of the present disclosure, for a single physiological characteristic data corresponding to the single detection sensor, the control signal may be generated based on the physiological characteristic data directly through the control component. For a plurality of different physiological feature data detected by the plurality of detection sensors, the intelligent glasses may directly send the plurality of different physiological characteristic data to a cloud server for processing the physiological characteristic data. The cloud server and the intelligent glasses may also work cooperatively. For example, the intelligent glasses process preliminary data and then send the processed data to the cloud server through the communication component to obtain the detection result, and then the control component of the intelligent glasses generates the control signal based on the detection result.

It can be understood that, for the processing of complicated data, by means of the communication component, a precise processing result is obtained by virtue of the cloud server. Then a precise control signal is obtained to control the treatment component to carry out treatment, which can improve the treatment effect. At the same time, the complicated data is processed through the cloud server, so that the power consumption of the intelligent glasses for processing complicated data can be reduced, thus prolonging the service time of a battery and alleviating the serious heating caused by the processing of the complicated data.

In some embodiments, the frame assembly includes a leg.

The intelligent glasses further includes a power supply component, located on the accommodating space at the tail portion of the leg, connected with the treatment component and the detection component, and configured to supply power to the treatment component and the detection component.

In the embodiments of the present disclosure, the power supply component is a rechargeable battery. The rechargeable battery includes a lead-acid rechargeable battery, a nickel-cadmium rechargeable battery or a lithium ion rechargeable battery. The embodiments of the present disclosure are not limited thereto. It can be understood that the power supply component supplies power to the treatment component and the detection component on the intelligent glasses, so that a detection function and a treatment function of the intelligent glasses can be realized.

In some embodiments, the frame assembly includes a lens frame.

The intelligent glasses further include a wireless induction coil, located on the lens frame or the leg and configured to charge the power supply component, or a connection component, located on the lens frame or the leg and configured to establish an electric connection with charging equipment. The charging equipment may include a mobile terminal, wearable electronic equipment or a charger.

The wireless induction coil may cooperate with a wireless charging coil, so as to realize wireless charging of the intelligent glasses. For example, the wireless induction coil may realize wireless charging by using a wireless power consortium QI. The connection component may be a connection wire. The charging equipment is connected through the connection wire to realize wired charging of the intelligent glasses.

The mobile terminal includes, but is not limited to, a smart phone, a smart tablet or a notebook computer. The wearable electronic equipment includes, but is not limited to, a smart necklace having power supply equipment or a smart hat having power supply equipment. The charging equipment includes, but is not limited to, mobile charging equipment or fixed charging equipment.

The embodiments of the present disclosure further provide a glasses box. The glasses box cooperates with the intelligent glass of the above one or more embodiments. The glass box includes a charging component. The charging component cooperates with the intelligent glasses, so as to charge the intelligent glasses through the glasses box.

It can be understood that since the intelligent glasses can be charged by means of the glasses box, the intelligent glasses are charged in time when the intelligent glasses are in low battery. As such, the service restriction caused by the low battery of the intelligent glasses is reduced.

In some embodiments, the charging component may include a charging interface and/or a wireless charging coil. In the embodiments of the present disclosure, the charging interface establishes an electrical connection with the power supply component of the intelligent glasses to realize charging of the intelligent glasses. The charging interface includes a micro-usb interface, a lightning interface or a type-c interface. The embodiments of the present disclosure are not limited thereto.

The wireless charging coil and the wireless induction coil of the intelligent glasses establish the electrical connection to realize charging of the intelligent glasses. The wireless charging coil includes an electromagnetic induction type wireless charging coil, and forms a charging region located in the glasses box. When the intelligent glasses are placed in the glasses box and the wireless induction coil of the intelligent glasses is aligned to the charging region in the glasses box, the charging can be realized, so that the use of a charging cable is avoided, and a convenient and quick charge can be achieved. Alternatively, the intelligent glasses may also be sucked on the glasses box for wireless charging in a contact manner.

In the embodiments of the present disclosure, the glasses box may further include an indication light for displaying a charging state of the intelligent glasses. Alternatively, the glasses box may further include a display screen for displaying the current power of the intelligent glasses.

It should be noted that "first" and "second" in the embodiments of the present disclosure are for the convenience of expression and distinguishing only, and do not have other special meanings.

Other embodiments of the present disclosure will be apparent to those skilled in the art from consideration of the specification and practice of the invention disclosed here. This application is intended to cover any variations, uses, or adaptations of the present disclosure following the general principles thereof and including such departures from the present disclosure as come within known or customary practice in the art. It is intended that the specification and examples be considered as exemplary only, with a true scope and spirit of the present disclosure being indicated by the following claims.

It should be understood that the present disclosure is not limited to the exact construction that has been described above and illustrated in the accompanying drawings, and that various modifications and changes can be made without departing from the scope thereof. It is intended that the scope of the present disclosure only be limited by the appended claims.

What is claimed is:

1. Intelligent glasses, comprising:
a frame assembly having an inner frame portion and an outer frame portion that is arranged around the inner frame portion so that one or more accommodating spaces are formed between the inner frame portion and the outer frame portion;
a detection component that is configured to detect physiological characteristics of a wearer;
a controller that is connected with the detection component and configured to acquire a control signal generated based on the physiological characteristics; and
a treatment component that is connected with the controller and configured to output treatment signals for treating the wearer based on the control signal, the treatment component including at least one of: a light source, a sonic wave emitter, a sound wave emitter, a magnetic wave emitter, an electrode emitter, and the treatment signals including at least one of: a phototherapy signal, a sonic wave signal, a sound wave signal, magnetic waves, or electromagnetic waves,
wherein each of the detection component, the controller, and the treatment component is located in the one or more accommodating spaces;
the detection component comprises a sweat detection sensor that is configured to detect sweat information in the physiological characteristics; the frame assembly comprises at least one lens frame and a nose pad connected to a side of the at least one lens frame; and
the sweat detection sensor is located in the one or more accommodating spaces at the nose pad,
wherein the sweat detection sensor is detachably connected to the nose pad.

2. The intelligent glasses according to claim 1, wherein the detection component further comprises at least one of:
an eyeball detection sensor that includes an infrared emitter and an infrared collector, the infrared emitter being configured to emit infrared light, the infrared collector being configured to collect infrared light reflected by an eyeball and to determine an eyeball motion information in the physiological characteristics based on the reflected infrared light;
a near infrared spectrum detection sensor that is configured to detect blood oxygen content information in the physiological characteristics; and
at least one electrode detection sensor that is configured to detect electric wave information in the physiological characteristics.

3. The intelligent glasses according to claim 2, wherein:
the frame assembly includes a lens frame and a leg that is hinged to the lens frame;
multiple said accommodating spaces are formed between the inner frame portion and the outer frame portion, and the near infrared spectrum detection sensor, the at least one electrode detection sensor, and the treatment component are distributed in different ones of the multiple accommodating spaces at the leg;
the treatment component is located in one of the multiple accommodating spaces at an end portion of the leg; and
the at least one electrode detection sensor is located between the treatment component and the near infrared spectrum detection sensor.

4. The intelligent glasses according to claim 2, wherein:
the detection component includes two electrode detection sensors; and
the near infrared spectrum detection sensor is located between the two electrode detection sensors.

5. The intelligent glasses according to claim 2, wherein:
the frame assembly includes a leg connected to another side of the at least one lens frame;
multiple said accommodating spaces are formed between the inner frame portion and the outer frame portion, and the eyeball detection sensor is located in one of the multiple accommodating spaces at the at least one lens frame on a side of the at least one lens frame where the leg is located.

6. The intelligent glasses according to claim 2, wherein the at least one electrode detection sensor further comprises at least one of an electrocardiogram detection sensor, an electromyogram detection sensor, or an electroencephalogram sensor.

7. The intelligent glasses according to claim 1, wherein:
the inner frame portion has an opening; and
the detection component is configured to send a detection signal to the wearer through the opening; or
the detection component is configured to receive the detection signal returned from the wearer through the opening.

8. The intelligent glasses according to claim 1, further comprising:
a connector having a first connection member and a second connection member that is hinged to the first connection member,
the frame assembly includes a lens frame that is connected with the first connection member and a leg that is connected with the second connection member, the leg being folded relative to the lens frame when the connector is folded at a hinged location of the first connection member and the second connection member.

9. The intelligent glasses according to claim 8, further comprising:
a first flexible printed circuit board covering the connector, the first flexible printed circuit board being folded along with the folding of the connector.

10. The intelligent glasses according to claim 8, wherein:
the connector includes a first connection port located on the first connection member, a second connection port located on the second connection member, and at least one connection line connected between the first connection port and the second connection port, and multiple said accommodating spaces are formed between the inner frame portion and the outer frame portion,
the intelligent glasses further includes:
a second flexible printed circuit board that is located in one of the multiple accommodating spaces at the lens frame and connected with the first connection port; and
a third flexible printed circuit board that is located in one of the multiple accommodating spaces at the leg and connected with the second connection port.

11. The intelligent glasses according to claim 8, wherein:
the connector is provided with a rotating shaft,
two first rotating holes spaced apart one from the other are formed in the first connection member,
one second rotating hole is formed in the second connection member and the second rotating hole is located between the two first rotating holes, and
the rotating shaft passes through the first rotating holes and the second rotating hole in sequence.

12. The intelligent glasses according to claim 1, wherein:
the frame assembly includes a leg, and
the intelligent glasses further include:
a communication component that is located on the leg, connected with the controller, configured to send the physiological characteristics detected by the detection component, and receive a returned detection result based on the physiological characteristics.

13. The intelligent glasses according to claim 12, wherein the communication component is electrically connected with a cloud server to send physiological characteristics to the cloud server.

14. The intelligent glasses according to claim 12, wherein the communication component comprises at least one of a Bluetooth communication component, a Wi-Fi communication component, a 5G communication component, a 6G communication component, or a near field communication (NFC) component.

15. The intelligent glasses according to claim 1, wherein:
the frame assembly includes a leg, and
the intelligent glasses further includes:
a power supply component that is located in the one or more accommodating spaces at a tail portion of the leg, connected with the treatment component and the detection component, and configured to supply power to the treatment component and the detection component.

16. The intelligent glasses according to claim 15, wherein:
the frame assembly includes a leg, and
the intelligent glasses further includes:
a wireless induction coil that is located on a lens frame or the leg and is configured to charge the power supply component; or
a connection component that is located on the lens frame or the leg and configured to establish an electric connection with charging equipment, the charging equipment including a mobile terminal, wearable electronic equipment, or a charger.

17. An electronic device, the electronic device comprising an intelligent glasses and glasses box that cooperates with the intelligent glasses, wherein the intelligent glasses comprises:
a frame assembly having an inner frame portion and an outer frame portion that are arranged around the inner frame portion to form one or more accommodating spaces between the inner frame portion and the outer frame portion;
a detection component that is configured to detect physiological characteristics of a wearer;
a controller that is connected with the detection component and configured to acquire a control signal generated according to the physiological characteristics; and
a treatment component that is connected with the controller and configured to output treatment signals for treating the wear based on the control signal, the treatment component including at least one of: a light source, a sonic wave emitter, a sound wave emitter, a magnetic wave emitter, an electrode emitter, and the treatment signals including at least one of a phototherapy signal, a sonic wave signal, a sound wave signal, magnetic waves, or electromagnetic waves,
wherein each of the detection component, the controller, and the treatment component is located in the one or more accommodating spaces,
the detection component comprises a sweat detection sensor that is configured to detect sweat information in the physiological characteristics; the frame assembly comprises at least one lens frame and a nose pad connected to a side of the at least one lens frame; and the sweat detection sensor is located in the one or more accommodating spaces at the nose pad,
the sweat detection sensor is detachably connected to the nose pad; and
wherein the glasses box includes a charging component that cooperates with the intelligent glasses to charge the intelligent glasses through the glasses box.

18. The electronic device according to claim 17, wherein the charging component comprises at least one of a charging interface or a wireless charging coil.

19. The electronic device according to claim 18, wherein the charging interface comprises at least one of a micro-usb interface, a lightning interface, or a type-c interface.

* * * * *